(12) United States Patent
Khan et al.

(10) Patent No.: US 10,709,400 B2
(45) Date of Patent: Jul. 14, 2020

(54) HEMODYNAMIC AND MORPHOLOGICAL PREDICTORS OF VASCULAR GRAFT FAILURE (71) Applicants: The Board of Trustees of the Leland Stanford Junior University, Stanford, CA (US); The Regents of the University of California, Oakland, CA (US)

(72) Inventors: Muhammad Owais Khan, Mountain View, CA (US); Andrew M. Kahn, San Diego, CA (US); Alison L. Marsden, Stanford, CA (US)

(73) Assignees: The Board of Trustees of the Leland Stanford Junior University, Stanford, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 16/502,264

(22) Filed: Jul. 3, 2019

(65) Prior Publication Data

US 2020/0008765 A1 Jan. 9, 2020

Related U.S. Application Data (60) Provisional application No. 62/694,166, filed on Jul. 5, 2018.

(51) Int. Cl.
*A61B 6/00* (2006.01)
*A61B 6/03* (2006.01)
*A61B 34/10* (2016.01)

(52) U.S. Cl.
CPC .............. *A61B 6/504* (2013.01); *A61B 6/032* (2013.01); *A61B 34/10* (2016.02); *A61B 2034/102* (2016.02); *G06T 2207/10081* (2013.01); *G06T 2207/30101* (2013.01)

(58) Field of Classification Search
CPC ................................ A61B 34/10; A61B 6/032
See application file for complete search history.

(56) References Cited

U.S. PATENT DOCUMENTS

2018/0085167 A1* 3/2018 Goyal ..................... A61B 34/20
2019/0240377 A1* 8/2019 Min ......................... A61L 27/18

FOREIGN PATENT DOCUMENTS

| CN | 104116563 | 10/2014 |
| WO | WO2018018033 | 1/2018 |

* cited by examiner

*Primary Examiner* — Edward Park
(74) *Attorney, Agent, or Firm* — Lumen Patent Firm

(57) ABSTRACT

A non-invasive method to predict post-surgery vascular graft failure is provided. Computer Tomography Angiography (CTA) images are obtained of a patient post-surgery. A personalized three-dimensional computer model of the patient is derived from the obtained CTA images. The personalized three-dimensional computer model distinguishes a Computational Fluid Dynamics (CFD) model coupled with a closed-loop Lumped Parameter Network (LPN). Post-surgery vascular graft predictors are calculated from the personalized three-dimensional computer model indicative, i.e. predictors, of the post-surgery vascular graft failure or vascular stenosis.

16 Claims, 8 Drawing Sheets

| | |
|---|---|
| Age, y | 83.7 ± 9.5 |
| Female, n (%) | 1 (7) |
| Body mass index, kg/m² | 25.2 ± 2.2 |
| Diabetes, n (%) | 7 (47) |
| Hypertension, n (%) | 14 (93) |
| Hyperlipidemia, n (%) | 14 (93) |
| LDL (mg/dL) | 66.1 ± 20.9 |
| Smoking history, n (%) | 6 (40) |
| Family history of CAD, n (%) | 11 (73) |
| Previous MI, n (%) | 14 (93) |
| LVEF < 35%, n (%) | 4 (27) |
| Heart Failure, n (%) | 13 (87) |
| Peripheral vascular disease, n (%) | 2 (13) |
| Stroke, n (%) | 1 (7) |

FIG. 6

| | |
|---|---|
| Total No. of SVGs | 40 |
| • Stented/Stenosed (>60%) | 17 |
| • Non-stenosed | 23 |
| Stenosed/Stented SVG Target Vessel (n=17) | |
| • Diagonal, n (%) | 2 (12) |
| • OM, n (%) | 10 (59) |
| • RCA, n (%) | 5 (29) |
| Non-Stenosed SVG target vessel (n=23) | |
| • LAD, n (%) | 4 (18) |
| • Diagonal, n (%) | 4 (18) |
| • OM, n (%) | 7 (30) |
| • RCA, n (%) | 7 (30) |
| • Ramus, n (%) | 1 (4) |
| No. of SVGs with Stents (N=5) | |
| • Diagonal, n (%) | 2 (40) |
| • OM, n (%) | 3 (60) |

FIG. 7

| | Parameter | Stenosed | | Non-Stenosed | | P | AUC | Cut-off | Sensi-tivity | Spec-ificity |
|---|---|---|---|---|---|---|---|---|---|---|
| | | Median | IQR | Median | IQR | | | | | |
| i | Curvature (1/cm) | 0.79 | 0.12 | 0.84 | 0.25 | 0.36 | 0.60 | 0.83 | 0.58 | 0.67 |
| | Tortuosity | 0.34 | 0.13 | 0.30 | 0.21 | 0.65 | 0.57 | 0.26 | 0.89 | 0.37 |
| | Length (cm) | 11.60 | 3.92 | 12.40 | 5.95 | 0.24 | 0.56 | 8.90 | 0.89 | 0.33 |
| | Area (cm²) | 0.090 | 0.041 | 0.094 | 0.057 | 0.78 | 0.51 | 0.10 | 0.42 | 0.72 |
| | Area* | 0.31 | 0.066 | 0.34 | 0.23 | 0.41 | 0.55 | 0.37 | 0.46 | 0.83 |
| ii | WSS (dyn/cm²) | 8.37 | 5.56 | 9.01 | 9.70 | 0.59 | 0.50 | 13.60 | 0.35 | 0.82 |
| | WSS* | 1.27 | 0.27 | 1.33 | 0.50 | 0.55 | 0.57 | 1.48 | 0.43 | 0.82 |
| | LSA | 0.0065 | 0.0090 | 0.0078 | 0.011 | 0.29 | 0.59 | 0.0093 | 0.43 | 0.76 |
| | OSI | 0.019 | 0.014 | 0.024 | 0.035 | 0.42 | 0.60 | 0.047 | 0.30 | 0.88 |
| | Flow (mL/s) | 0.76 | 0.71 | 0.63 | 0.33 | 0.66 | 0.53 | 0.50 | 0.83 | 0.41 |
| iii | WSS$_{sten}$ (dyn/cm²) | 9.71 | 4.16 | 8.77 | 10.92 | 0.55 | 0.51 | 13.23 | 0.37 | 0.86 |
| | WSS$_{sten}$* | 1.22 | 0.42 | 1.36 | 0.71 | 0.013 | 0.70 | 1.30 | 0.68 | 0.68 |
| | OSI$_{sten}$* | 0.0051 | 0.018 | 0.011 | 0.016 | 0.36 | 0.62 | 0.0058 | 0.71 | 0.54 |

FIG. 8

HEMODYNAMIC AND MORPHOLOGICAL PREDICTORS OF VASCULAR GRAFT FAILURE

CROSS-REFERENCE TO RELATED APPLICATIONS

This application claims priority from U.S. Provisional Patent Application 62/694,166 filed Jul. 5, 2018, which is incorporated herein by reference.

STATEMENT OF GOVERNMENT SPONSORED SUPPORT

This invention was made with Government support under contract HL123689 awarded by the National Institutes of Health. The Government has certain rights in the invention.

FIELD OF THE INVENTION

The invention relates to methods and systems to predict vascular graft failure.

BACKGROUND OF THE INVENTION

Coronary artery bypass grafting (CABG) is a common treatment for patients with multi-vessel obstructive coronary artery diseases. Saphenous vein graft (SVGs), harvested from patients' inner thigh, are typically used, but have high failure rates. Nearly 50% of the SVGs fail within 10 years, leading to further interventions with potentially higher risk of morbidity and mortality. Abnormal wall shear stresses (WSS) and wall biomechanics play a key role in mechanobiological stimuli that contribute to SVG failure. However, these stimuli are difficult to obtain non-invasively through current imaging modalities. This invention advances the art by developing a model and predictors of SVG failure.

SUMMARY OF THE INVENTION

A method is provided to non-invasively predict post-surgery vascular graft failure. One or more Computer Tomography Angiography (CTA) images are obtained of a patient post-surgery. The surgery included a vascular graft. In one specific example the surgery included a vein graft or more specifically a saphenous vein graft. In one example, the surgery is a Coronary Artery Bypass Graft (CABG) surgery. The images obtained from the patient includes at least the vascular graft of the patient.

A personalized three-dimensional computer model of the patient is derived from the obtained CTA images. The personalized three-dimensional computer model includes at least the vascular graft. Specifically, the personalized three-dimensional computer model distinguishes a Computational Fluid Dynamics (CFD) model coupled with a closed-loop Lumped Parameter Network (LPN). More specifically, the CFD model represents a coronary anatomy, an aortic anatomy and hemodynamic profiles. In one example, the LPN models a coronary physiology. In another example, the LPN represents the physiology of the four heart chambers of the patient, a systemic circulation and a coronary circulation. In yet another example, the LPN models the out-of-phase behavior of the coronary versus the systemic circulation. In still another example, the method includes matching parameters of the LPN model to match standard-of-care invasive clinical measurements. These clinical measurements could be a cardiac output, a heart rate, a systolic blood pressure, a diastolic blood pressure, a left ventricle ejection fraction, or any combination thereof.

From the personalized three-dimensional computer model one or more vascular graft predictors are calculated that are predictors of the post-surgery vascular graft failure or vascular stenosis. Once these predictors have been computed they are outputted to the operator or user of the method. The method could be a computer processing pipeline executed in an automatic fashion by a computer processor, which could also be part of a system.

In one embodiment, a vascular graft predictor is a wall shear stress of the vascular graft. In another embodiment, a vascular graft predictor is a normalized wall shear stress of the vascular graft. In yet another embodiment, a vascular graft predictor is a curvature of the vascular graft. In still another embodiment, a vascular graft predictor predicts and outputs the adequacy of the vascular graft post-surgery.

In one embodiment, the one or more vascular graft predictors are hemodynamic predictors, which could be an oscillatory shear index, a low shear area, a flow rate or a velocity of the vascular graft.

In one embodiment, the one or more vascular graft predictors are anatomic predictors, which could be a tortuosity, a length, an area or an area ratio of the vascular graft.

More specifically, to the processing of the images, a three-dimensional model of patient's anatomy is segmented and reconstructed from obtained images, which may include, but not limited to, the aorta, the left and right common carotid arteries, the subclavian artery, the left and right coronary arteries and all coronary sub-branches, the left internal mammary artery grafts, the radial artery grafts and SVGs.

More specifically, to the processing of the images, three-dimensional models are used to characterize the anatomy of all segmented branches. Anatomic characterization can include curvature, tortuosity, torsion, length, cross-sectional area and bifurcation angles.

More specifically, to the three-dimensional models, a tuned closed-loop Lumped Parameter Network Model (LPN), and echocardiography measurements are used to compute accurate hemodynamics.

More specifically, to the LPN, which can include circuit blocks (e.g. resistors, capacitors) representing the four chambers of the heart, systemic and coronary circulations. Parameters of CL-LPN can be tuned from all non-invasive parameters during clinical examination, such as from echocardiography. These parameters can include cardiac output, heart rate, systolic and diastolic blood pressure.

More specifically, to the hemodynamics which can include performing computational simulations on computers to determine velocity, pressures and shear stresses. The simulations can include three-dimensional models segmented from medical images, tuned LPN model.

DETAILED DESCRIPTION

This invention provides a method and system using computational fluid dynamics (CFD)-derived hemodynamic and CTA-based anatomic predictors of SVG failure. While the definition of failure is not universal, it is either characterized as complete occlusion of the SVG or as presence of a clinically significant stenosis. We have used the latter definition for the purposes of this invention.

For the purposes of this invention, a retrospective study was designed to review a cohort of N=650 patients. From this population, patients were selected who had at least one moderate-to-severely stenosed and one non-stenosed SVG, so that patients served as their own control. Exclusion criteria included: i) patients with only LIMA/RIMA grafts, ii) SVGs not visualized on CTA due to complete or partial occlusion, iii) SVGs that appeared aneurysmal and patulent. Also excluded were patients whose CTA showed significant motion and metal artifacts. After aforementioned exclusion criteria, a total of N=15 CABG patients with N=40 SVGs were identified. Within each patient, the SVGs were tagged as either stenosed or non-stenosed and the region of stenosis was marked for local comparison. Table 1 and Table 2, appended herein infra, summarize the clinical characteristics of the patients, and the SVG patency status by target vessel, respectively.

Clinical Data

Image Segmentation, Model Reconstruction and Mesh Generation

Figure 1A:
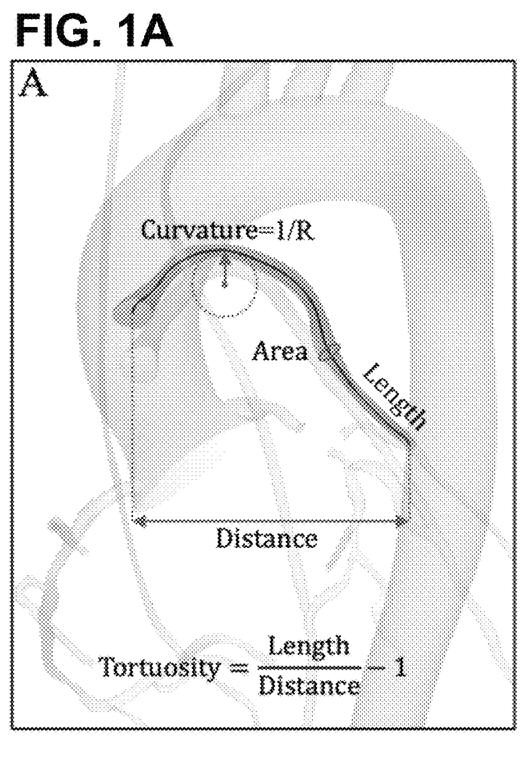
FIG. 1A shows according to an exemplary embodiment of the invention anatomic parameters computed on a representative model reconstructed from a Computer Tomography Angiography (CTA). Measurements were made at 200 points along the saphenous vein graft (SVG) centerline to compute all anatomic parameters.

Three-dimensional patient-specific anatomic CABG models were segmented from CTA images using the open-source SimVascular software; www.simvascular.org. All segmentations were performed by a trained radiology technician at the 3D and Quantitative Imaging Laboratory at Stanford University, who was blinded to the hypothesis of the study. Details of the segmentation and reconstruction methodology have previously been described. A representative example of the 3D model is shown in FIG. 1A. Centerlines were identified along the coronary arteries, aorta, aortic branch vessels and bypass grafts. Lumens were segmented on 2D slices perpendicular to the centerline and lofted together to generate a 3D patient-specific model.

Figure 1B:
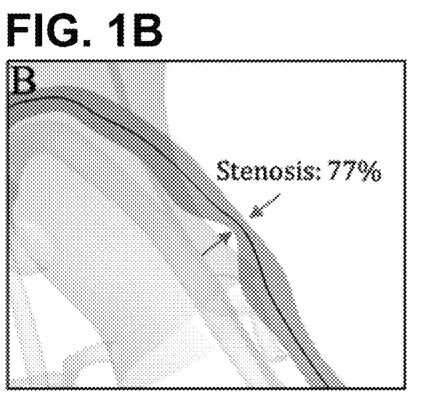
FIG. 1B shows according to an exemplary embodiment of the invention stenosis with a severity of 77% area reduction near the mid-portion of the SVG.
Figure 1C:
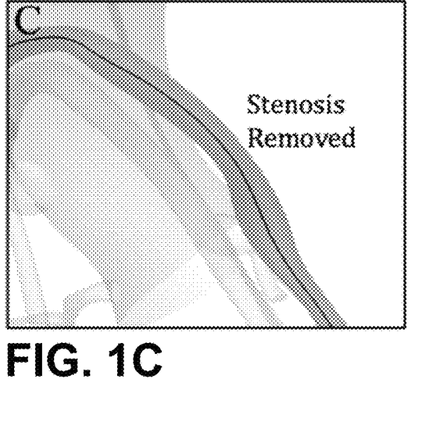
FIG. 1C shows according to an exemplary embodiment of the invention pre-stenosed reconstruction through virtual removal of the stenosis.

Since immediate post-operative images are not available as a standard-of-care, virtually removed was the stenosis to approximate a pre-stenosed state of the SVG. In SimVascular, the lumen shape was interpolated proximally and distal to the stenosis to approximate the pre-stenosed shape of the vessel. FIGS. 1B and 1C show the stenosed and virtually-reconstructed segments, respectively.

Reconstructed models were discretized into linear tetrahedral elements using MeshSim (Simmetrix Inc., Clifton Park, N.Y.) for CFD simulations. Three boundary layers and variable mesh resolution were assigned: 0.3 mm to aorta and aortic branch vessels, 0.035 mm to the native coronaries and 0.02 mm to the SVGs. The average mesh size was 4.4 million elements ranging from 3.1 to 6.3 million elements, reflecting the variability in SVG and native coronary sizes and extent of CFD model domain. These mesh resolutions provided mesh-independent hemodynamic quantities.

Morphological Parameter

Three-dimensional models were processed to automatically compute SVG morphological parameters using the Vascular Modeling Toolkit; www.vmtk.org. As shown in FIG. 1A, curvature, tortuosity, length and area were computed by discretizing the SVG centerline into 200 equidistant points along the SVG centerline. Curvature was defined as the inverse of the radius of the osculating circle that locally approximated the curve and thus, was a local measure of deviation from a straight line. Tortuosity was defined as the ratio of SVG length to Euclidian distance between the two anastomosis points. Since area mismatch has previously been proposed as a predictor SVG failure, we also computed area ratio of the SVG and target coronary vessel (area$_{svg/target}$).

Multi-Scale Computational Fluid Dynamics Simulations

Figure 2:
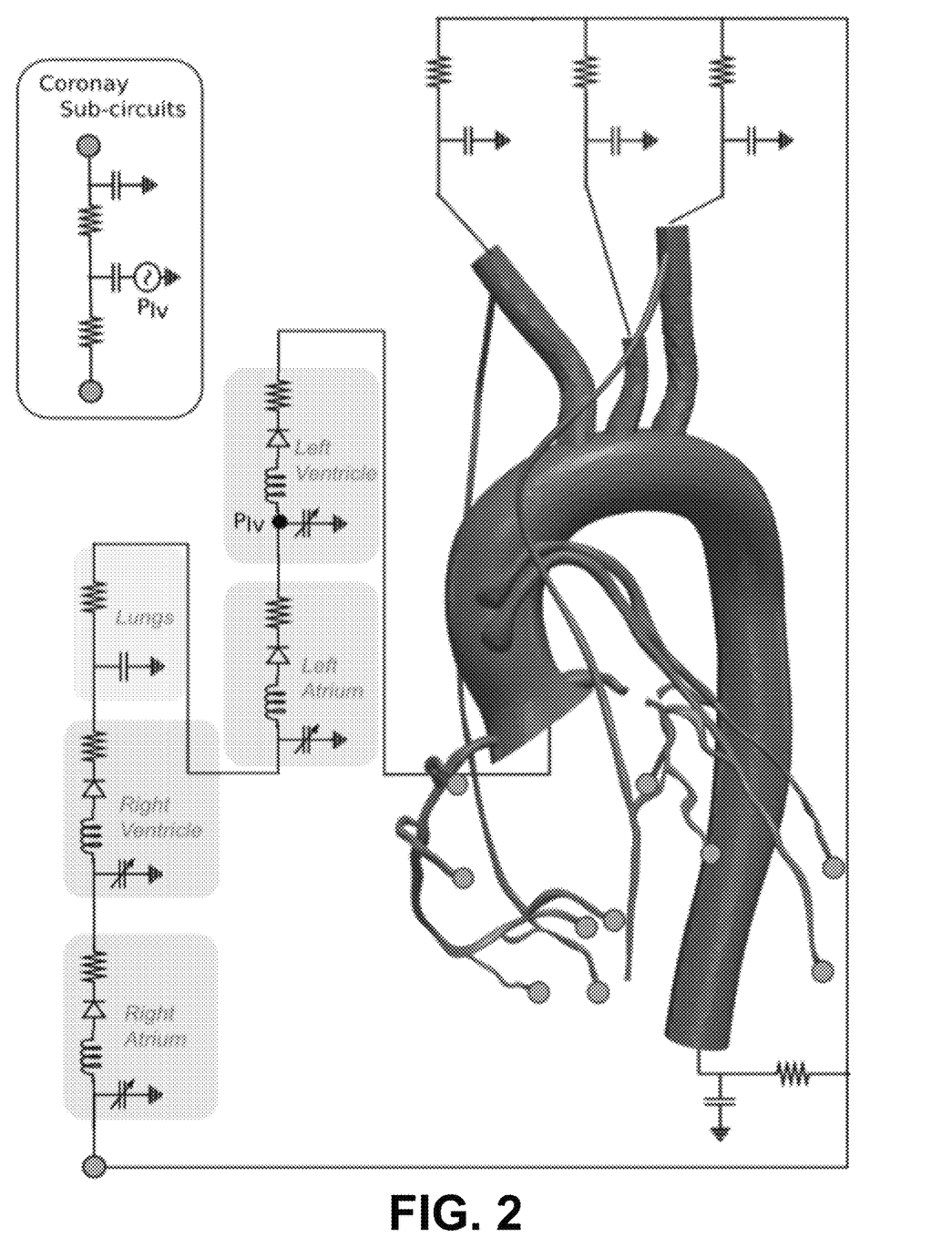
FIG. 2 shows according to an exemplary embodiment of the invention a schematic view of a multi-scale patient-specific model of the coronary circulation, coupling a closed-loop Lumped Parameter Network (LPN) to 3D model. The LPN parameters, such as resistances, capacitances, were tuned to match clinical targets to within 10%.

Details of the simulation methodology have previously been provided [1]. Briefly, fluid-structure interactive (FS) simulations were conducted, where the vessel wall thicknesses and material properties were assigned based on literature values and wall thickness approximated as 10% of vessel diameter. Circulation outside of the 3D domain, including the heart, systemic circulation, and microcirculation, was modeled using a closed-loop lumped parameter network (LPN) as shown in FIG. 2 and described in [2]. The LPN was required to adequately model the coronary physiology, particularly the out-of-phase behavior of coronary versus the systemic circulation, not possible through conventional RCR (Windkessel) circuit. An automated tuning framework was used to match the LPN parameters to match standard-of-care invasive clinical measurements, including cardiac output, heart rate, systolic and diastolic blood pressure, left ventricle ejection fraction. It was assumed that 4% of the total cardiac output was assigned to the coronary arteries, with 70%-30% flow split to the left and the right coronary tree, respectively. Within each tree, the flow was further distributed to each vessel based by scaling the resistance and capacitance to the area. All simulations were run for six cycles to wash out initial transients and 1,000 time-steps were used per cardiac cycle. The last cardiac cycle was used for processing all of the hemodynamic quantities.

Hemodynamic Parameter

Simulation results were post-processed to compute parameters of presumed biological relevance, particularly time-averaged wall shear stress (WSS) and oscillatory shear index (OSI), low shear area (LSA). To reduce the error in WSS due to flow rate assumptions, we also normalized WSS (WSS*) by the analytically computed WSS ($WSS_{analytical}$) value based on average flow rate and diameter.

The WSS was computed using the following formula:

$$WSS = \frac{1}{T}\int_0^T |WSS_i| dt$$

where $WSS_i$ is the instantaneous shear stress vector and T is the cardiac cycle.

The OSI was computed using the following formula:

$$OSI = \frac{1}{2}\left\{1 - \frac{\left|\int_0^T WSS_i dt\right|}{\int_0^T |WSS_i| dt}\right\}$$

The LSA was defined as the areas of the SVG wall exposed to a WSS below 10% of the mean WSS of the vessel.

The $WSS_{analytical}$ was computed as following:

$$WSS_{analytical} = \frac{4vQ}{\pi R^3}$$

Where v is the viscosity, Q the flow rate and R the radius of the vessel.

Statistical Analysis

Statistical analysis was performed on morphological and hemodynamic parameters to identify the difference between stenosed and non-stenosed SVGs. A Shapiro-Wilk test was performed to check for normality. Since all variables were found to be non-normally distributed, a two-sided paired Wilcoxon test was used, and results were reported as median and interquartile range (IQR). Some patients had >1 non-stenosed SVGs (multiple controls). Therefore, each stenosed SVG was paired with a randomly selected non-stenosed SVG making all pairs independent. The process was repeated 200 times, and the mean p-value and confidence intervals were calculated. If the mean p-value was <0.05, the difference between stenosed and non-stenosed pairs was considered statistically significant. Repeating the random selections 400 times did not show differences. Therefore, 200 repetitions were deemed sufficient. Receiver operating characteristics (ROC) analysis was performed on all parameters to determine the optimal thresholds separating ruptured and unruptured groups by calculating the area under the ROC curve (AUC).

Results

Figure 8:
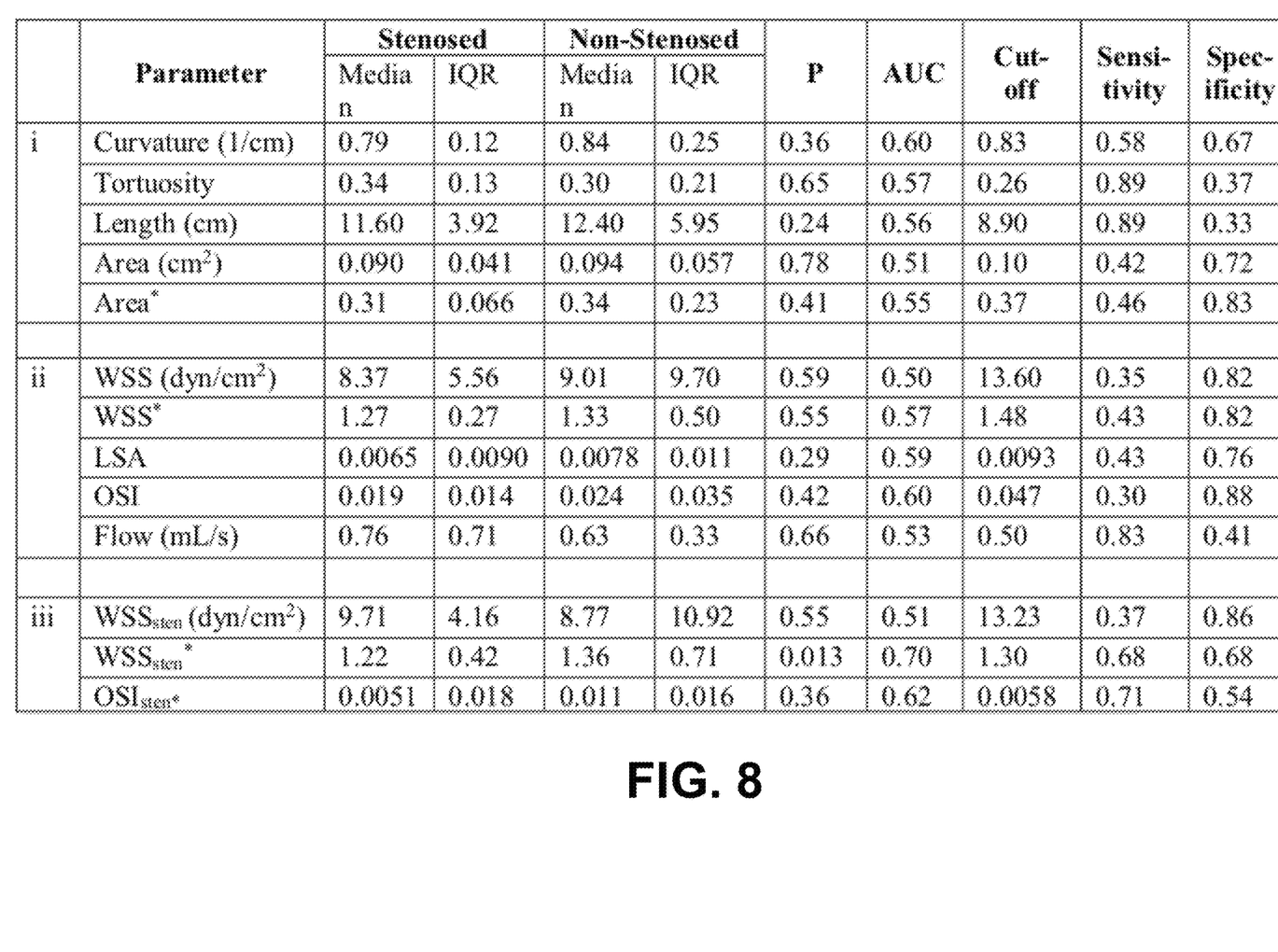
FIG. 8 shows according to an exemplary embodiment of the invention Table 3 results from univariate statistical analysis, showing median and interquartile range (IQR). i) and ii) correspond to anatomic and hemodynamic parameters, respectively, averaged over the complete length of the SVG. iii) corresponds to hemodynamic parameters over the stenosis region compared to the same region of the non-stenosed SVG. WSS, wall shear stress; WSS*, normalized wall shear stress; LSA, low shear area; OSI, oscillatory shear index.

Table 3 as shown infra summarizes the results. As seen from the table, none of the anatomic or hemodynamic predictors, computed for the entire length of the graft, showed statistical significance. However, it was observed that the region of stenosis had significantly lower normalized WSS ($WSS_{sten}$*) compared to the control segment on the normal SVG in the same patient. The area under the curve (AUC) had a value of 0.7, which is comparable to other predictors of graft failure such as mean graft flow rate, albeit with slightly higher sensitivity values.

Figure 3:
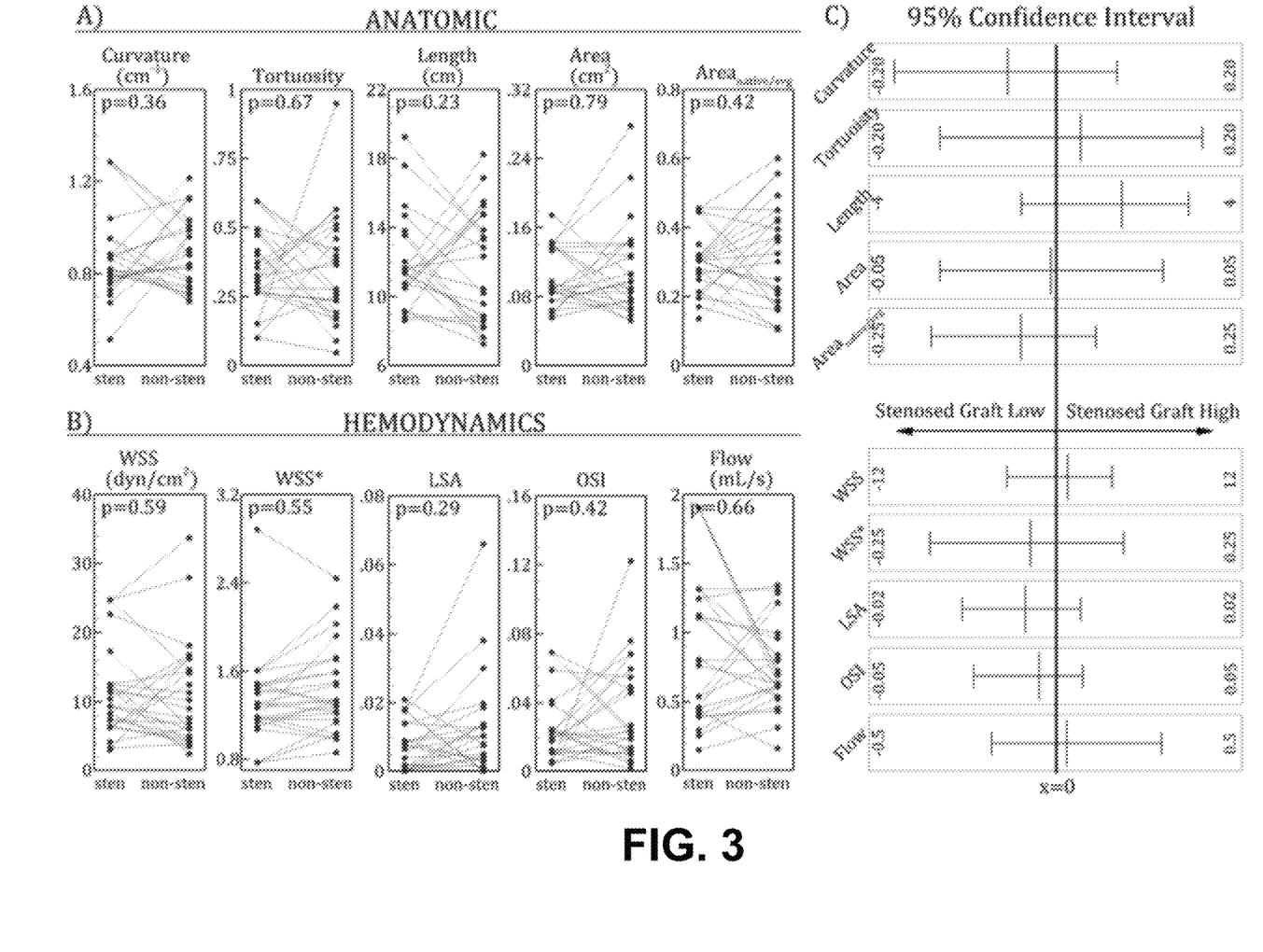
FIG. 3 shows according to an exemplary embodiment of the invention paired plots of anatomic (A) and hemodynamic (B) parameters, averaged over the whole length of the saphenous vein graft (SVG). C) 95% confidence interval. sten, stenosed; non-sten, non-stenosed; WSS, wall shear stress, WSS*, normalized wall shear stress; LSA, low shear area; OSI, oscillatory shear index.
Figure 4:
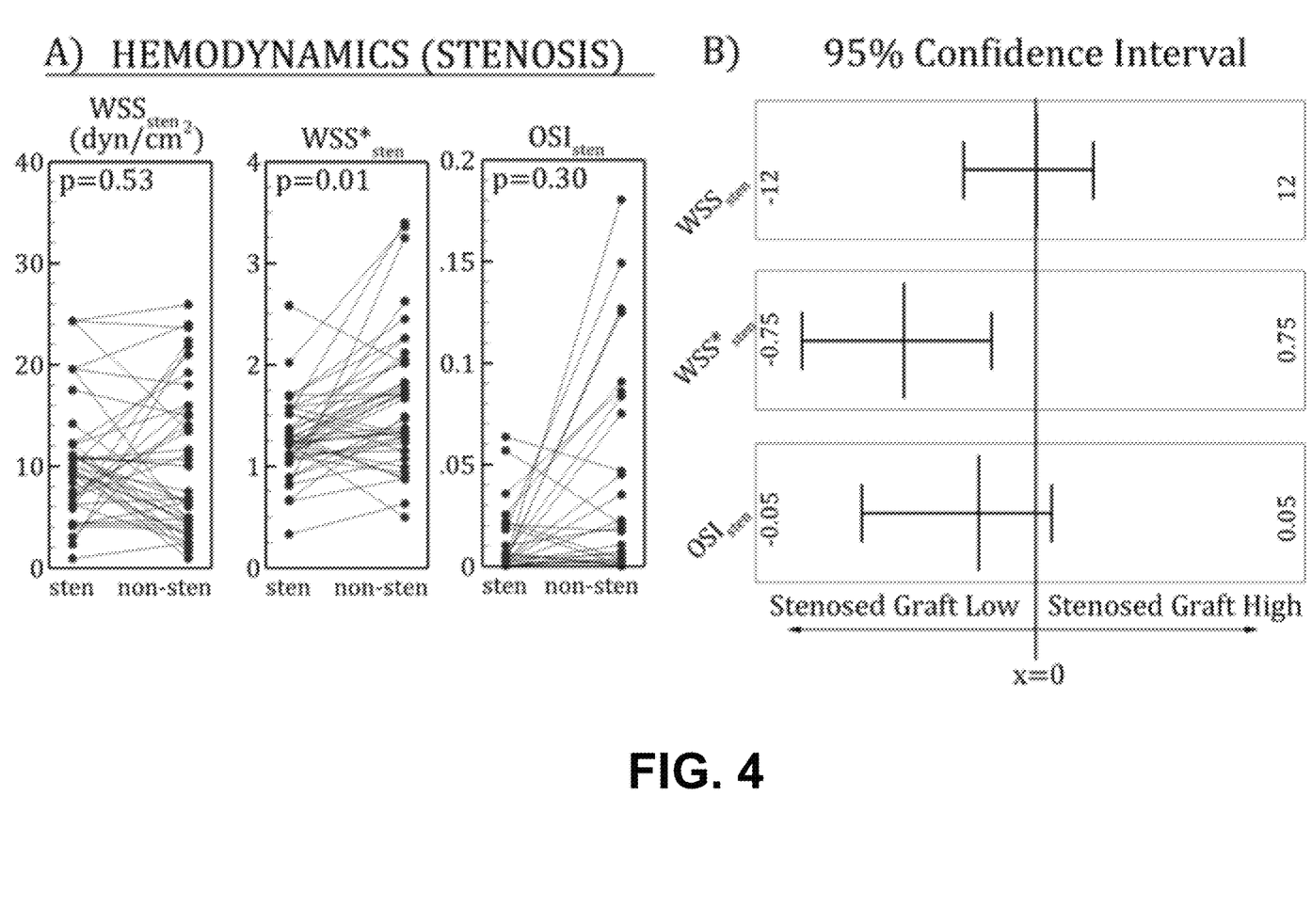
FIG. 4 shows according to an exemplary embodiment of the invention paired plots of hemodynamic (A) parameters measured only in the region of stenosis. The controls were considered the same region on the non-stenosed SVG in the same patient. C) 95% confidence interval. sten, stenosed; non-sten, non-stenosed; WSS, wall shear stress, WSS*, normalized wall shear stress; OSI, oscillatory shear index.
Figure 5:
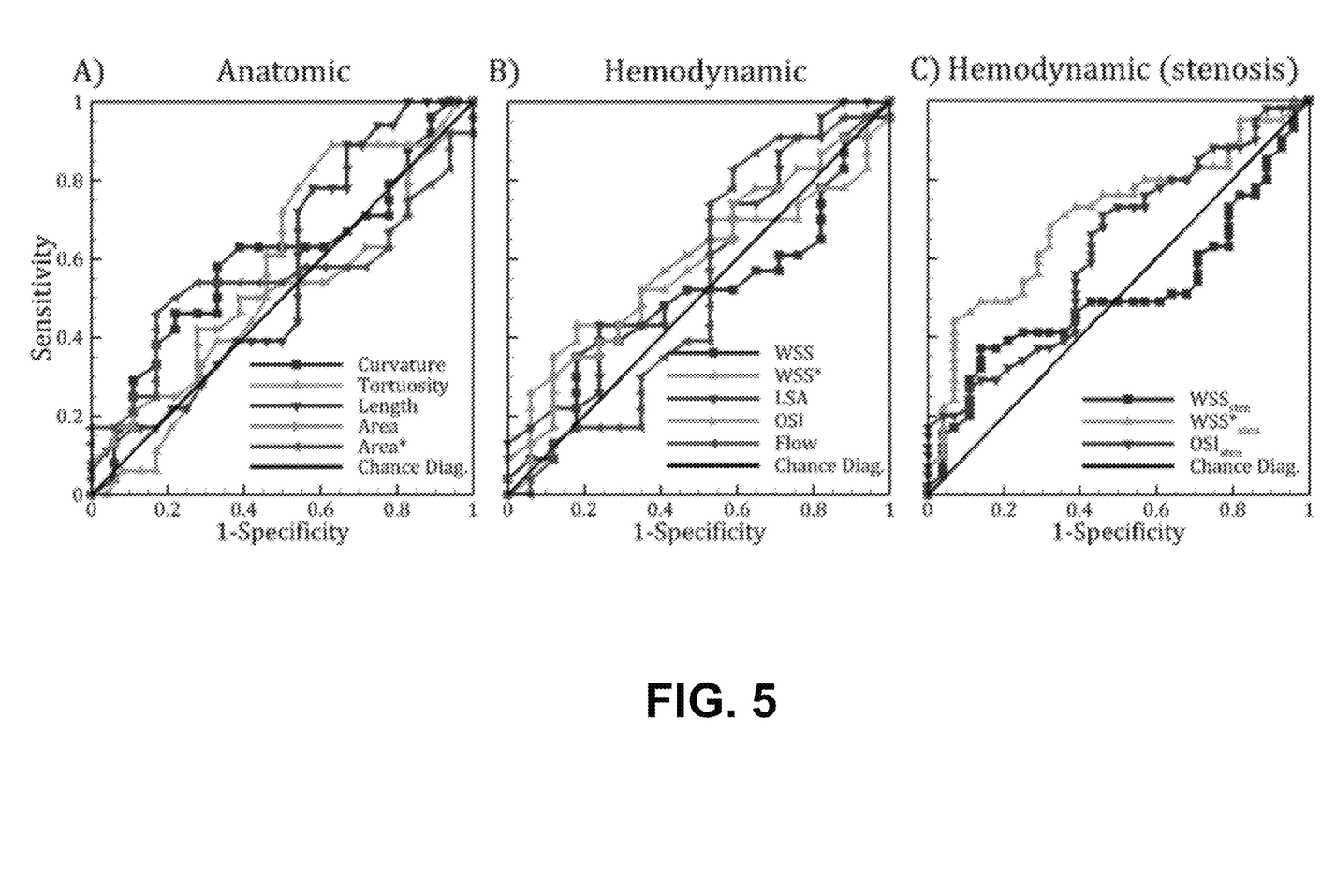
FIG. 5 shows according to an exemplary embodiment of the invention the receiver operating characteristic curve of anatomic (A) and hemodynamic (B & C) parameters. The diagonal line corresponds to the line of no-discrimination of chance diagonal. sten, stenosed; non-sten, non-stenosed; WSS, wall shear stress, WSS*, normalized wall shear stress; LSA, low shear area; OSI, oscillatory shear index.
Figure 6:
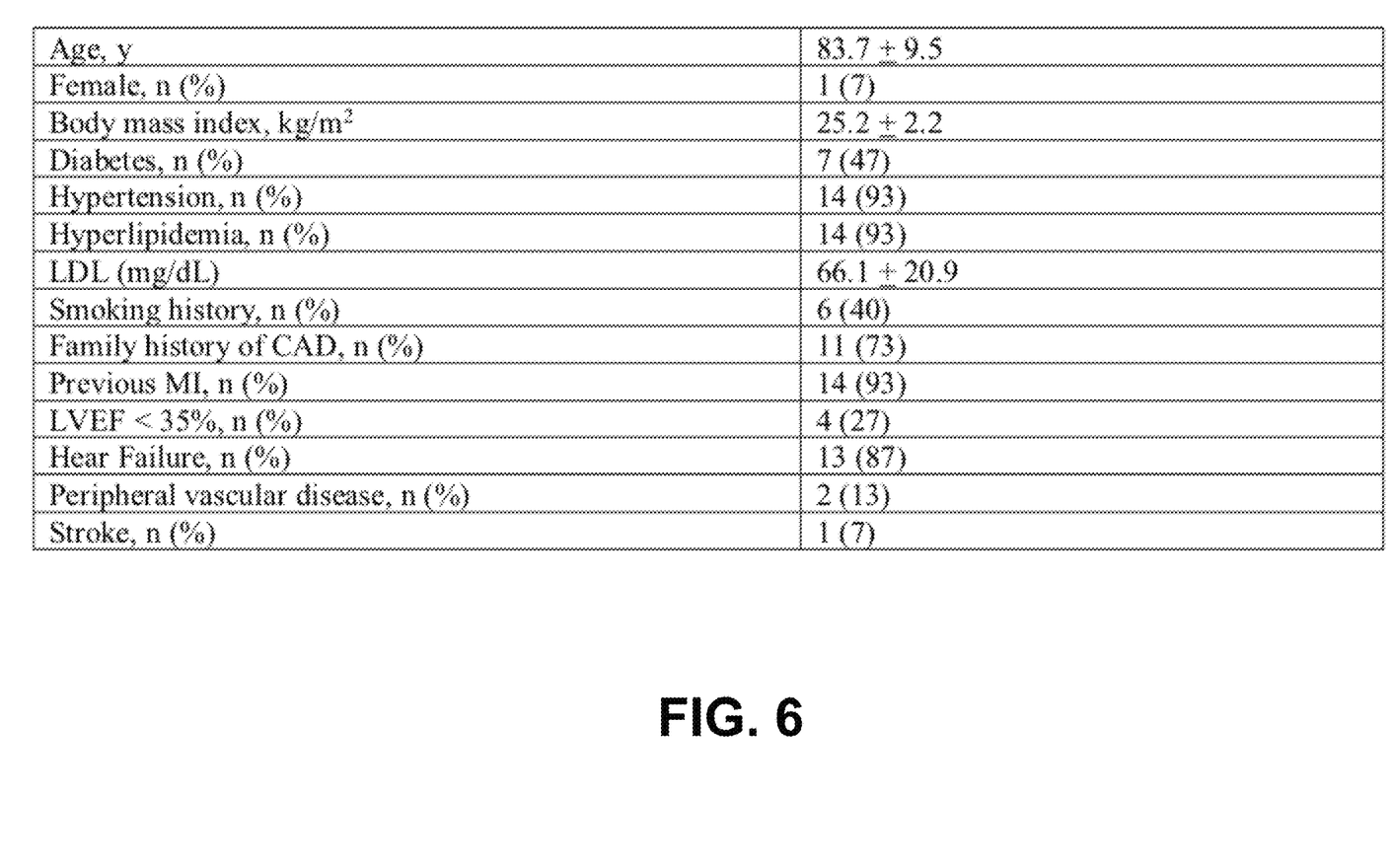
FIG. 6 shows according to an exemplary embodiment of the invention Table 1 with demographic and clinical characteristic of study population (n=15). Data are mean and standard deviation when appropriate. LDL, low-density lipoprotein; CAD, coronary artery disease; LVEF, left ventricle ejection fraction.
Figure 7:
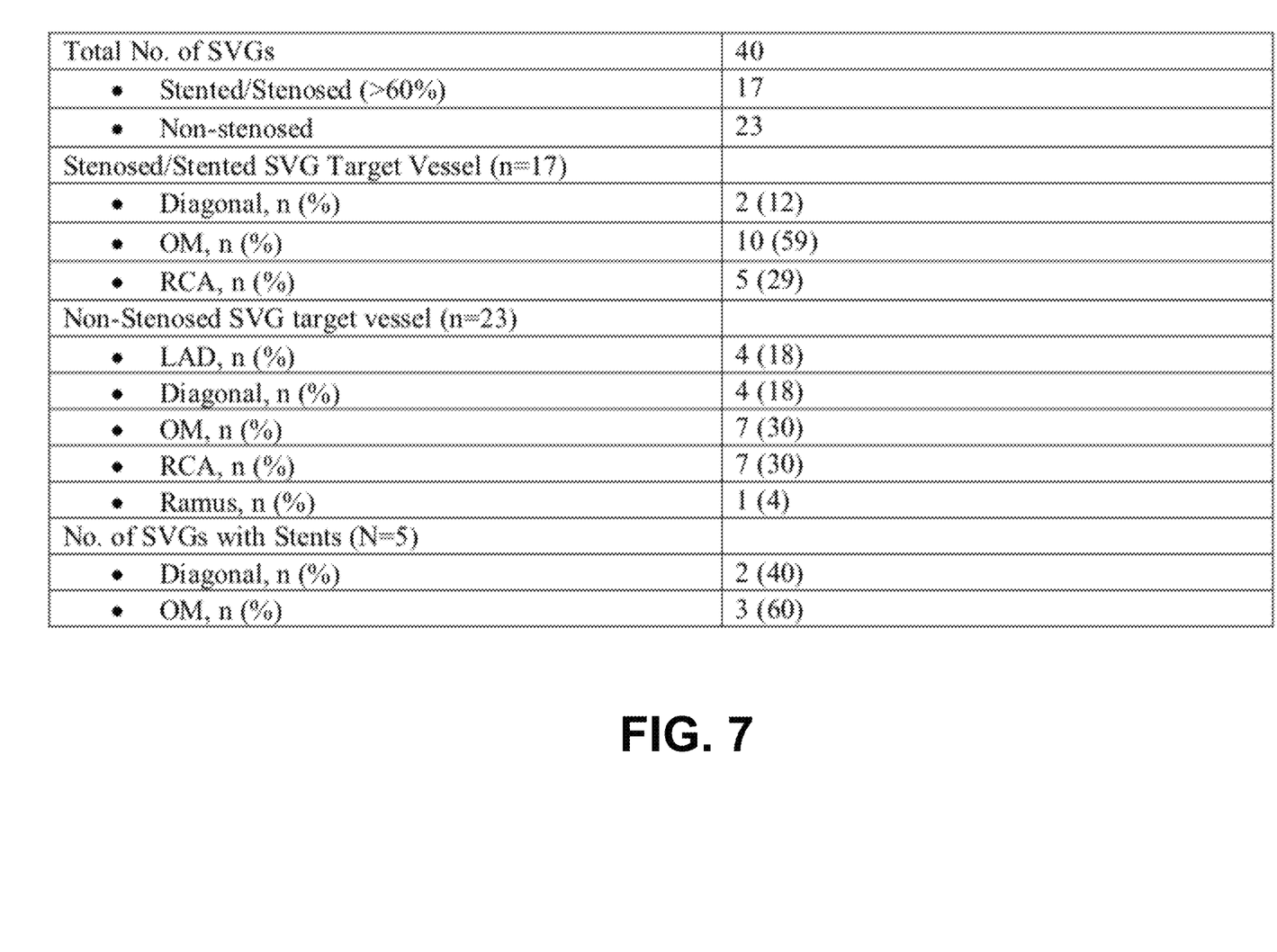
FIG. 7 shows according to an exemplary embodiment of the invention Table 2 SVGs target vessels and patency status. OM, obtuse marginal; RCA, right coronary artery; LAD, left anterior descending artery.

Similar observations are made from the paired plots shown in FIG. 3 for the entire length of the graft, and FIG. 4 for the stenosis segment only. Particularly, from FIG. 4, it was noted that $WSS*_{sten}$ showed consistently lower values for the stenosed segment compared to the non-stenosed segment. Interestingly, while p-value for the $OSI_{sten}$ did not indicate statistical significance, the confidence intervals showed that $OSI_{sten}$ may have some predictive value.

Significance

Currently, there are no strong non-invasive predictors of saphenous vein graft (SVG) failure. CTA imaging and angiography can potentially provide anatomic predictors, but those have limited predictive value. With this invention and results, the inventors have demonstrated that computational fluid dynamics (CFD) combined with novel LPN modeling techniques have the potential to non-invasively predict regions of clinically significant stenosis, which could lead the complete occlusion of the SVG. Particularly, a new parameter (WSS*) has shown potential to be of relevance in the mechano-biological process that may be associated with SVG stenosis.

REFERENCES

[1] A. B. Ramachandra, A. M. Kahn, and A. L. Marsden, "Patient-Specific Simulations Reveal Significant Differences in Mechanical Stimuli in Venous and Arterial Coronary Grafts," *J. Cardiovasc. Transl. Res.*, vol. 9, no. 4, pp. 279-290, 2016.

[2] J. S. Tran, D. E. Schiavazzi, A. B. Ramachandra, A. M. Kahn, and A. L. Marsden, "Automated tuning for parameter identification and uncertainty quantification in multiscale coronary simulations," *Comput. Fluids*, vol. 142, pp. 128-138, 2016.

What is claimed is:

1. A method of non-invasively predicting post-surgery vascular graft failure, comprising:
   (a) obtaining Computer Tomography Angiography (CTA) images of a patient post-surgery, wherein the surgery included a vascular graft, and wherein the images comprise at least the vascular graft of the patient; and
   (b) deriving from the obtained CTA images a personalized three-dimensional computer model of the patient, wherein the personalized three-dimensional computer model comprising at least the vascular graft, wherein the personalized three-dimensional computer model comprises a Computational Fluid Dynamics (CFD) model coupled with a closed-loop Lumped Parameter Network (LPN);

(c) calculating one or more vascular graft predictors from the personalized three-dimensional computer model, wherein the one or more vascular graft predictors are indicative of the post-surgery vascular graft failure or vascular stenosis; and (d) outputting the one or more vascular graft predictors.

2. The method as set forth in claim 1, wherein the Computational Fluid Dynamics (CFD) model represents a coronary anatomy, an aortic anatomy and hemodynamic profiles.

3. The method as set forth in claim 1, wherein the closed-loop Lumped Parameter Network (LPN) models a coronary physiology.

4. The method as set forth in claim 1, wherein the closed-loop Lumped Parameter Network (LPN) represents a physiology of the four heart chambers of the patient, a systemic circulation and a coronary circulation.

5. The method as set forth in claim 1, wherein the closed-loop Lumped Parameter Network (LPN) models the out-of-phase behavior of the coronary versus the systemic circulation.

6. The method as set forth in claim 1, further comprising matching parameters of the closed-loop Lumped Parameter Network (LPN) model to match standard-of-care invasive clinical measurements, wherein the including clinical measurements are a cardiac output, a heart rate, a systolic blood pressure, a diastolic blood pressure, a left ventricle ejection fraction, or any combination thereof.

7. The method as set forth in claim 1, wherein the vascular graft is a vein graft.

8. The method as set forth in claim 1, wherein the vascular graft is a saphenous vein graft.

9. The method as set forth in claim 1, wherein the surgery is a Coronary Artery Bypass Graft (CABG) surgery.

10. The method as set forth in claim 1, wherein the one or more vascular graft predictors is a wall shear stress of the vascular graft.

11. The method as set forth in claim 1, wherein the one or more vascular graft predictors is a normalized wall shear stress of the vascular graft.

12. The method as set forth in claim 1, wherein the one or more vascular graft predictors is a curvature of the vascular graft.

13. The method as set forth in claim 1, wherein the one or more vascular graft predictors predict and output adequacy of the vascular graft post-surgery.

14. The method as set forth in claim 1, wherein the one or more vascular graft predictors are hemodynamic predictors, wherein the hemodynamic predictors are an oscillatory shear index, a low shear area, a flow rate or a velocity of the vascular graft.

15. The method as set forth in claim 1, wherein the one or more vascular graft predictors are anatomic predictors, wherein the anatomic predictors are a tortuosity, a length, an area or an area ratio of the vascular graft.

16. The method as set forth in claim 1, wherein the method is a computer processing pipeline executed in an automatic fashion by a computer processor.

* * * * *